United States Patent [19]

Taylor

[11] Patent Number: Plant 6,816

[45] Date of Patent: May 23, 1989

[54] PLUM

[75] Inventor: James W. Taylor, Dinuba, Calif.

[73] Assignee: Ito Packing Co., Inc., Reedley, Calif.

[21] Appl. No.: 137,375

[22] Filed: Dec. 22, 1987

[51] Int. Cl.[4] ..... A01H 5/03

[52] U.S. Cl. ..... Plt./38

[58] Field of Search ..... Plt./38

*Primary Examiner*—Robert E. Bagwill

*Attorney, Agent, or Firm*—Dennis B. Haase

[57] ABSTRACT

A new and distinct variety of plum tree of a red fleshed, cling stone fruit variety, attractive in appearance and maturing in the mid-season period.

1 Drawing Sheet

BACKGROUND OF THE VARIETY

The present invention relates to a new and distinct variety of plum tree, which I refer to as Sweet Gypsy, of a red fleshed, cling stone fruit, attractive in appearance maturing in the mid-season period, which was developed from a continued fruit breeding program.

ORIGIN AND ASEXUAL REPRODUCTION OF THE NEW VARIETY

This novel plum variety was derived from an ongoing fruit breeding program dedicated to the improvement of plums to enhance consumer quality and market acceptability. Propagation was effected by taking the seed from the Mariposa variety (U.S. Plant Pat. No. 111) which was stratified and grown to a height of about 18 inches. These seedlings were then bud grafted into dehorned orchard trees in the experimental orchard of Ito Packing Co., Inc., Reedley, Calif., for testing and selection. Each clone was budded into several limbs to make sure that it propagated true to type.

SUMMARY OF THE NEW VARIETY

The instant variety, developed through the above method, was selected because of its excellent eating quality, which is similar to that of its parent, or the Oriental Satsuma type. However, the novel plum of the present invention ripens about one week ahead of its parent and is much more attractive in appearance.

BRIEF DESCRIPTION OF THE DRAWING

The accompanying drawing illustrates typical specimens of the fruit and foliage of my new variety as grown in the San Joaquin Valley of California. Two specimens are shown, one of which is in side elevation, while the other shows a bottom view; yet another specimen is a sectional side elevation illustrating the internal texture and color, as well as the exposed stone. A characteristic twig and individual leaves are shown.

DETAILED DESCRIPTION

The following is a detailed description of my new plum variety with color reference being to the Maerz and Paul Dictionary of Colors, except in instances where terminology having generally accepted meaning is employed.

Parentage: Open pollenated seedling of the variety Mariposa.

Propagation: Maintains its distinguishing characteristics through several bud grafts.

Locality where grown and observed: Near Reedley, Calif. County of Fresno, Calif.

TREE

Size: Large, spreading, open.

Vigor: Vigorous, productive.

Regularity of bearing: Regular bearer.

Trunk: Medium size; medium texture.

Branches: Spreading, average in length and stockiness.

Leaves:

- *Color.*—Top side, 32C11; underside, 31H9.
- *Size.*—Average length of $2\frac{7}{8}$ inches; average width of $\frac{7}{8}$ inch; medium thickness.
- *Shape.*—Oval to obovate.
- *Marginal form.*—Finely serrate.
- *Glandular characteristics.*—Wanting on many leaves but frequently one small globose gland on either side of the leaf blade near the petiole attachment.
- *Petiole.*—Slightly longer than most other varieties of the *P. salicina* species.
- *Stipules.*—Often wanting, but may be present on young growth.

Flower bud: Medium, white.

Flower: Medium size, white.

- *Anthers.*—Yellow.

Time of full bloom: With variety Santa Rosa.

FRUIT

Maturity: When described, firm ripe, June 15, 1986; June 28, 1987.

Date of first picking: June 28, 1987.

Date of last picking: July 10, 1987.

Size: Average axial length, $1\frac{7}{8}$ inches; average transverse width in suture plane, $2\frac{1}{8}$ inches.

Form: Essentially round but slightly compressed at the base. Characteristic rounded protrusion in the area around the apex.

- *Suture.*—Smooth with very little depression.
- *Ventral surface.*—Round.
- *Cavity.*—Round, shallow.
- *Base.*—Flatted slightly.
- *Apex.*—Smooth although may be slightly recessed in some fruit.
- *Axial diameter.*—$2\frac{1}{4}''$.
- *Transverse diameter.*—$2\frac{1}{2}''$.

Skin:

- *Thickness.*—Medium thick, medium texture.

*Tendency to crack.*—None observed.

*Bloom.*—Light.

*Color.*—Reddish purple (7A6), darkening to 55J11 as the fruit matures and deepening to 55L11 in the final stages of maturity. Characteristic dots occur sparsely over most of the surface.

Flesh:

*Texture.*—Firm, juicy.

*Color.*—Red (4L2) in general but lighter around the pit (4J3) tending to be a cream color with red cast in some small areas. As the fruit becomes soft ripe the red color deepens to a dark red (55L12).

*Juice.*—Abundant.

*Flavor.*—Very sweet with pleasant acid balance.

*Aroma.*—Quite pronounced.

*Fibers.*—Few.

*Ripening.*—Evenly.

*Eating quality.*—Excellent.

Stone:

*Adherence to flesh.*—Generally clinging but separates from the fruit around portions of the pit in some fruits.

*Size.*—Average thickness, $\frac{1}{4}$ inch; average width, $\frac{5}{8}$ inch; average length, $\frac{3}{4}$ inch.

*Form.*—Oval.

*Hilum.*—Small, oval.

*Dorsal edge.*—Shallow groove, interrupted irregularly.

*Ventral edge.*—Wing continuous from near base to about $\frac{1}{4}$ inch from the apex.

*Surface.*—Irregularly pitted.

*Color.*—Brown.

Use: Market, juice.

Keeping quality: Excellent.

Shipping quality: Excellent.

Resistance to disease: Although this novel variety of plum tree possesses the described characteristics as a result of the growing conditions in Fresno County, Calif. in the central portion of the San Joaquin Valley, it is to be understood that variations of the usual magnitude in characteristics incident to growing condition, fertilization pruning and pest control are to be expected.

Having thus described and illustrated my new variety of plus tree, what is claimed as new and desired to be secured by Letters Patent is:

1. A new and distinct variety of plum tree with fruit of a red fleshed cling type, substantially as herein shown and described, and having an early ripening quality, making it available for the early season, with fruit of an excellent quality with a particularly distinctive and attractive deep red quality.

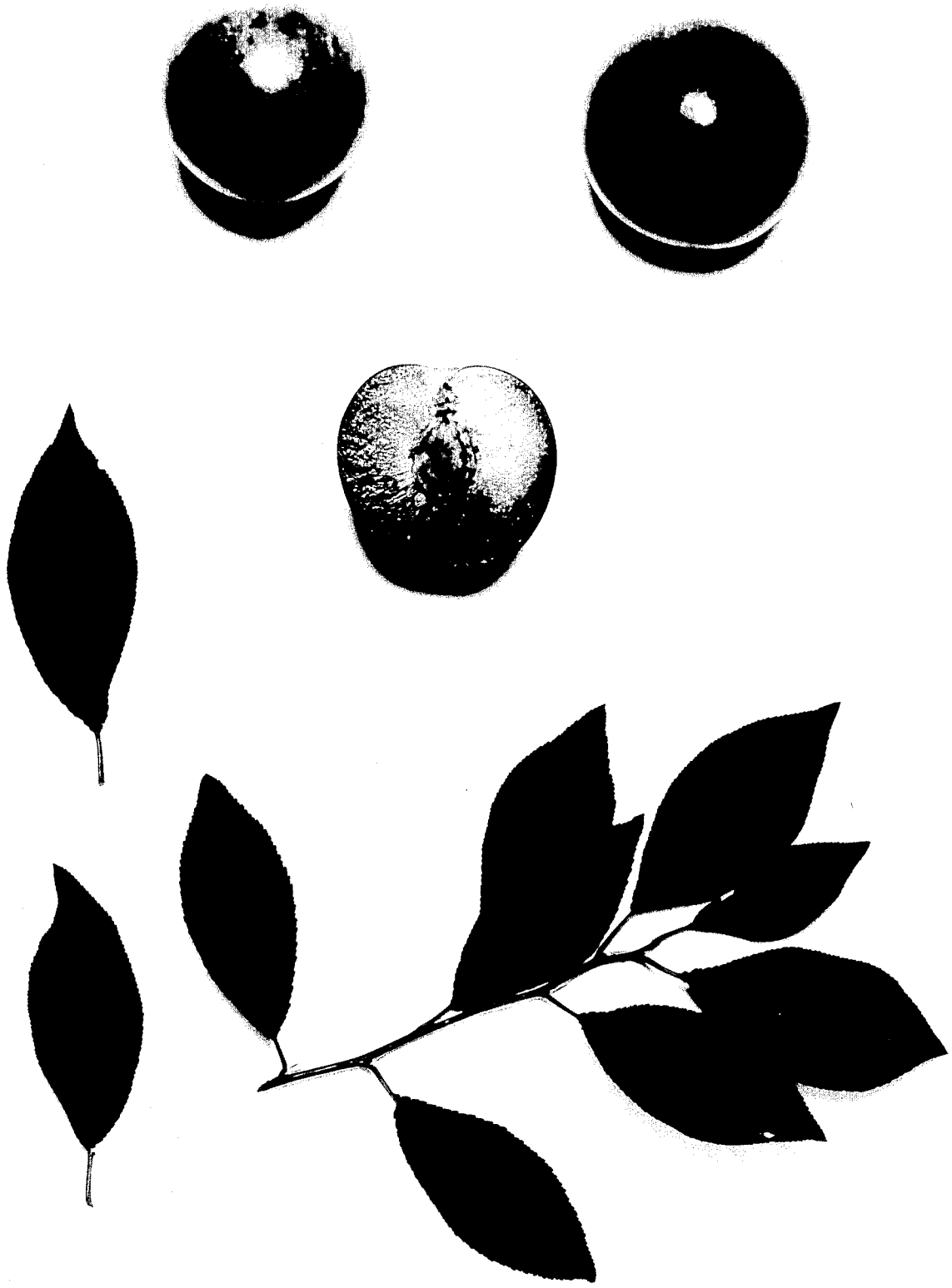

* * * * *